Figure 1:
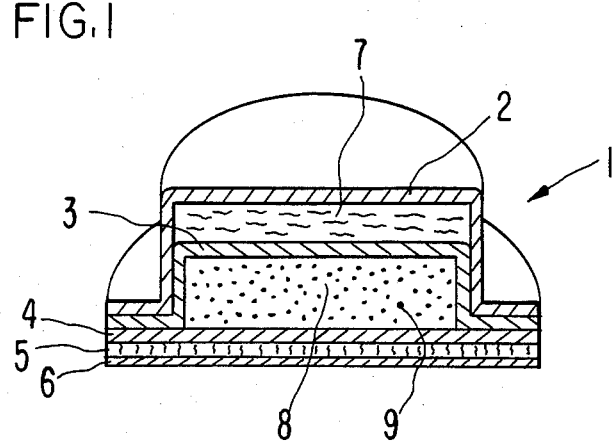

United States Patent [19]

Gale et al.

[11] Patent Number: 4,645,502
[45] Date of Patent: Feb. 24, 1987

[54] TRANSDERMAL DELIVERY OF HIGHLY IONIZED FAT INSOLUBLE DRUGS

[75] Inventors: Robert M. Gale, Los Altos; David J. Enscore, Sunnyvale, both of Calif.

[73] Assignee: ALZA Corporation, Palo Alto, Calif.

[21] Appl. No.: 730,713

[22] Filed: May 3, 1985

[51] Int. Cl.⁴ .............................................. A61K 9/00
[52] U.S. Cl. .................................................. 604/896
[58] Field of Search ............................. 604/890–897; 128/136

[56] References Cited

U.S. PATENT DOCUMENTS 3,797,494 3/1973 Zaffaroni .............................. 604/897
4,379,454 4/1983 Campbell et al. .................... 604/897
4,460,372 7/1984 Campbell et al. .................... 604/897

*Primary Examiner*—C. Fred Rosenbaum
*Assistant Examiner*—Jerome R. Smith, Jr.
*Attorney, Agent, or Firm*—Steven F. Stone; Edward L. Mandell; Paul L. Sabatine

[57] ABSTRACT

A medical device for the transdermal delivery of highly ionized, fat insoluble drugs comprises an aqueous drug reservoir having a physiological pH, said reservoir preferably being a gel maintained in an impermeable receptacle by a highly permeable support member disposed between the gel and a permeable contact adhesive. A permeation enhancer reservoir delivers a permeation enhancer to the skin through the aqueous reservoir and through a permeation enhancer release rate controlling membrane which is permeable to the permeation enhancer and impermeable to the drug and water. In a preferred embodiment the permeation enhancer release rate controlling membrane forms at least a portion of said receptacle.

13 Claims, 2 Drawing Figures

TRANSDERMAL DELIVERY OF HIGHLY IONIZED FAT INSOLUBLE DRUGS

FIELD OF THE INVENTION

This invention relates to medical devices for delivering drugs to the body through intact skin and more particularly for delivering the ionized form of highly ionized, fat insoluble drugs.

BACKGROUND OF THE INVENTION

Devices that deliver drugs through the skin for absorption into the body have been known for some time. For example, U.S. Pat. No. 3,249,109 describes a two-layer topical dressing that consists of an adhesive base made of drug-containing hydrated gelatin with a fabric backing layer. This type of device could be considered a "skin-controlled" device because the system delivers an excess of drug to the skin and the rate of absorption is controlled by the permeability of the skin at the application site which can vary over relatively wide ranges from site-to-site and individual-to-individual. In order to deliver transdermal drugs having a relatively narrow therapeutic range, and for which such wide variations could not be tolerated, "system-controlled" delivery devices were developed which deliver drugs transdermally at rates which are controlled primarily by the delivery device to reduce or eliminate the variations in drug input rate associated with variations in skin permeability. For example, U.S. Pat. No. 3,598,122 describes a multilayer adhesive bandage formed of a backing layer, a drug reservoir layer and a contact adhesive layer, and includes means for metering the rate at which the drug is released to the skin. Other representative system controlled transdermal drug delivery devices are described in U.S. Pat. Nos. 3,797,494 and 4,379,454, the latter of which teaches controlling the rate at which a drug is absorbed through the skin by controlling the rate at which a permeation enhancer for the drug is delivered to the skin. (All of the aforementioned U.S. patents are incorporated herein by reference.) In addition, Black, "Transdermal Drug Delivery Systems", U.S. Pharmacist, November 1982, pp. 49-78, provides additional background information regarding commercially available transdermal drug delivery systems and a reasonably complete summary of the factors involved in percutaneous absorption of drugs may be found in Arita, et al, "Studies on Percutaneous Absorption of Drugs", Chem. Phar. Bull., Vol. 18, 1970, pp. 1045-1049; Idson, "Percutaneous Absorption", J. Phar. Sci., Vol. 64, No. 6, pp. 910-922; and Cooney, Advances in Biomedical Engineering, Part 1, Chapter 6, "Drug Permeation Through Skin: Controlled Delivery for Topical of Systemic Therapy", Marcel Dekker, Inc., New York and Basel, 1980 pp. 305-318.

Although the transdermal drug delivery route is rapidly becoming a preferred delivery route for a wide variety of drugs, transdermal delivery is not without its problems. A large number of drugs are oil-insoluble and in aqueous solutions exist, depending on pH, either as the unionized acid or base or in the ionized salt form. The unionized forms of most drugs are generally more permeable through the skin than the ionized drug making it easier to achieve, either with or without permeation enhancers, blood levels which are capable of producing the desired therapeutic effects. (See R. J. Scheuplein, et al., "Permeability of the Skin", Physiological Reviews, Vol. 51, No. 4, October 1972, pp. 702-747, particularly 729-735). Unfortunately, the pH of aqueous solutions of a free base or acid is usually below 3 for the acid or above 10 for the base, and transdermal delivery at these pH's may cause discomfort and/or irritation to the skin of the recipients. Adjusting the pH of solutions of these drugs to a more physiologically acceptable level (e.g., 5-8) results in a substantial proportion of the drug being converted to the nonpermeable, ionized form. As a result, prior to our invention we are unaware of any transdermal drug delivery system which is capable of delivering the ionized form of highly ionized, fat insoluble drugs at rates adequate to produce desired therapeutic effects.

It is accordingly an object of this invention to provide a medical device for transdermal drug delivery adapted to deliver the ionized form of a highly ionized, fat insoluble drug.

It is another object of this invention to provide a transdermal drug delivery device capable of delivering a highly ionized, fat insoluble drug from an aqueous reservoir.

It is another object of this invention to provide a transdermal drug delivery device in which a highly ionized, fat insoluble drug is delivered at a substantially physiological pH.

It is another object of this invention to provide a transdermal drug delivery device capable of delivering the ionized form of a fat insoluble drug at a substantially constant rate.

It is another object of this invention to provide reservoir compositions useful in the aforementioned drug delivery devices.

Figure 2:
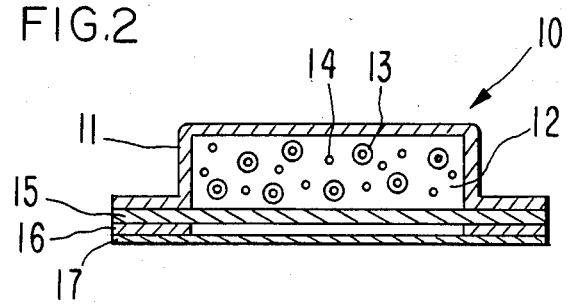

These and other objects and advantages of this invention will be readily apparent from the following description with reference to the accompanying drawings wherein:

FIG. 1 is a section through a perspective view of a schematic representation of a preferred embodiment of a transdermal drug delivery device according to this invention, and FIG. 2 is a cross-section view through another embodiment of this invention.

DESCRIPTION OF THE INVENTION

The specific drugs used are not critical to this invention and as used herein the term "drug" is to be construed in its broadest sense as a material which is intended to produce some beneficial effect on the organism to which it is applied. As used herein, a drug in its acid or basic form is considered to be "oil-insoluble" if the solubility of the drug in mineral oil is less than about 100 $\mu$g/g. A drug is considered to be "highly ionized" when the percent ionization of the drug in an aqueous drug reservoir is at least about 95%. This occurs when the $pK_a$ of the drug differs from the pH of the reservoir by an absolute value of at least 1.3. The $pK_a$ of a drug is the pH of an aqueous solution in which 50% of the drug is in the ionized salt form and 50% is in the unionized base or acid form. Since physiological pH of the skin is in the range of approximately 5.5-7.2; the $pK_a$ for acidic drugs according to this invention is lower than about 4.2 and for basic drugs, higher than 8.5. Representative drugs meeting these criteria include, without limitation, acidic drugs such as the sodium or other salts of indomethacin, acetazolamide, methazolamide, and acetylsalisylic acid, for example, and salts or acid salts of basic drugs such as naltrexone HCl, naloxone HCl, nalbuphine HCl, phenylephrine HCl, chlorpheniramine maleate, phenylpropanolamine HCl, clonidine HCl, dextromethophan HBr, atropine sulfate, fentanyl citrate, apomorphine sulfate, propranolol HCl, lidocaine HCl, tetracycline HCl, oxytetracycline HCl, tetracaine HCl, dibucaine HCl, terbutaline sulfate, and brompheniramine maleate, for example.

Referring now to FIG. 1, a preferred embodiment of a transdermal delivery device 1 according to this invention is shown. This system is specifically adapted to deliver the ionized, salt form of a highly ionized, oil-insoluble acidic or basic drug from an aqueous reservoir.

The preferred embodiment comprises an impermeable backing 2 bonded about its periphery to a permeation enhancer release rate controlling member 3 and spaced apart therefrom in its central portion to define a permeation enhancer reservoir 7. Member 3 is similarly bonded about its periphery to a porous support member 4 and spaced apart therefrom in its central portion to define an aqueous drug reservoir 8. A contact adhesive layer 5 which layer is permeable to the drug and enhancer is preferably bonded to the surface of porous support 4 and a strippable release liner 6, adapted to protect adhesive 5 prior to use and to be readily removed therefrom, is also provided. To permit transport of drug and enhancer to the skin, the adhesive may be porous or hydrated to be permeable to the drug and enhancer for example. If impermeable to drug and enhancer the adhesive is, located or otherwise adapted to impose no significant resistance to drug and permeation enhancer transport to the skin. In a preferred embodiment, an in-line, porous polyacrylate adhesive is utilized in layer 5. If an hydratable contact adhesive formulation were used, the adhesive would be equilibriated with at least about 10 weight percent water to permit transport of ionized drug. It should be recognized, however, that if a peripherally located adhesive is used, it need not be porous or permeable. Also, if desired, an adhesive overlay or some other means such as buckles, belts, or elastic bands could be used to maintain the transdermal delivery system 1 on the skin in which case, if properly packaged, layers 5 and 6 could be omitted. Such a system might be desirable, for example, if the drug adversely affected the adhesive properties of the adhesive layer or if the drug were highly soluble in the adhesive.

Aqueous reservoir 8 contains at least 50%, and preferably substantially more, water containing the drug 9 dispersed therethrough, preferably at a level above saturation. Typically the reservoir will be in the form of a gel which may also contain stabilizing agents, other excipients and additives. A buffering agent may also be present if required to maintain the drug reservoir at physiological pH.

The permeation enhancer release rate controlling membrane 3 controls the rate of release of the permeation enhancer from the reservoir 7 to the skin. Porous substrate 4 functions as a physical support for the gelled reservoir and the substrate should be sufficiently porous so that it imposes substantially no resistance to the transport of drug and permeation enhancer to the skin.

In this regard, viscosity of the aqueous reservoir 8 is related to the porosity of the substrate 4 in that it should be sufficiently viscous so that the aqueous reservoir 8 will not readily flow through the substrate 4. The amount of gelling or other thickening agent used is not critical but should be the amount required to produce a viscosity in the reservoir 8 sufficient to prevent the reservoir from migrating or otherwise leaking or oozing through the porous substrate. Porous adhesive 5 is likewise selected to provide substantially no resistance to drug or enhancer release. It is a principal function of the substrate 4 to provide a support to which the adhesive 5 can be applied since it is difficult in many cases to provide a good bond between the porous adhesive 5 and the aqueous medium within reservoir 8.

Typically, the rate controlling membrane 3 will be a hydrophobic membrane which is capable of controlling the rate of release of the permeation enhancer from reservoir 7 while simultaneously preventing either water or the ionized drug from diffusing or otherwise migrating into enhancer reservoir 7. Thus, upon standing, the aqueous drug reservoir 8 will contain a saturation level of the permeation enhancer.

The materials used in the fabrication of elements 2, 4, 5 and 6 can be selected within very wide limits since they perform primarily structural functions. Thus, the impermeable backing can be any material which has the desired flexibility, impermeability and insolubility with respect to the permeation enhancer and may either be a single element or a metalized or composite coated element. Typical materials include, without limitation, ethylene vinyl acetate copolymers (EVA), polyesters, metalized polyesters, polyethylenes, polycarbonates, polyvinyl chlorides, polyvinylidene fluoride, polysulfones, or laminates of the above such as metalized polyester/EVA or medium density polyethylene/ EVA, for example.

The porous substrate 4 is preferably a soft, open-mesh, hydrophobic, fibrous material but may also be a non-fibrous, porous or sponge-like material, it being merely required that the substrate perform its functions of being bondable to the adhesive and maintaining the gelled aqueous material within the reservoir without providing any significant resistance to the transport of drug and permeation enhancer therethrough. Typical materials include spun laced polyester, spun-laced polyolefin coated polyester, spun bonded polyethylene, spun laced polyethylene or EVA, microporous polypropylene, microporous polycarbonate, woven nylon, rayon or polyester cloths, and open cellular polyethylene or polyurethane foams, for example.

The porous adhesive is preferably a polyacrylate contact adhesive (such as the Norwood 17C porous adhesive) or any other suitable porous adhesive. Alternatively, the adhesive could be a non-porous contact adhesive which is applied about the periphery leaving the center portion beneath reservoir 8 substantially free of adhesive. In that case, any biocompatible content adhesive could be applied, porous or not. Typical adhesive compositions include silicone adhesives, polyacrylates, polyisobutylene-mineral oil adhesives, tackified styrene-isoprene-styrene block copolymers (SIS), tackified EVA contact adhesives, polyacrylamides and various hydratable, hot melt or emulsified (water borne) adhesive compositions, for example.

The strippable backing member likewise can be any material known to the art and may be the same as or different from the material used to provide the impermeable backing 2. The basic requirement for layer 6 is that it be substantially impermeable to the passage of components from the reservoir and be readily removed from the adhesive 5 without destruction of the integrity of the device. As noted above, if adhesive 5 is not used to maintain the device on the skin, the device could be packaged in a close fitting impermeable pouch or bag and layer 6 could also be omitted.

With respect to the gelled aqueous drug reservoir, it is intended that water be the continuous phase. For that reason, the reservoir should be at least 50% and preferably over 70% water. The gelling agent used to thicken the reservoir can be any of a wide variety of gelling agents, such as silica, particulate porous polyisoprene, bentonite clay, various gums such as agar, traganths, polysaccharides, cellulosic materials such as hydroxyethyl cellulose, hydroxypropyl cellulose or hydroxypropyl methyl cellulose and polyacrylates, for example. The basic requirements are that the gelling agent is non-reactive with the drug and does not substantially interfere with the ready diffusion of the materials from the device. A relatively wide degree of flexibility in the amount of gelling agent used is available since the required viscosity varies inversely with the pore size selected for the substrate. A general range of approximately 1% to 10% by weight of these gelling agents is normally adequate.

The concentration of the drug within the aqueous reservoir can be varied within relatively wide ranges. Although preferable, it is not always necessary that the drug be present at the saturation concentration with an excess of undissolved drug. This is because, according to this invention, the rate at which the drug is delivered through the skin is controlled primarily by the rate of permeation enhancer delivery. Thus, it is contemplated that the drug may initially be present in the reservoir, either at, above or below the saturation level of the drug in the aqueous medium.

The drug reservoir may also contain a buffer to maintain the pH of the solution in the desired range during the drug delivery period. Suitable buffers should, of course, be unreactive with the other components of the system and should preferably form an ion-pair with the drug in which the ionic moiety of the buffer is no less permeable through the skin than the drug moiety. Suitable buffers for acid drugs and basic drugs include, without limitation, phosphates, citrates, ascorbates and carbonates, for example.

Membrane 3 is selected to be substantially impermeable to the flow of water and drug from reservoir 8 into the permeation enhancer reservoir 7 and to have that degree of permeability to the permeation enhancer to permit the rate at which the permeation enhancer is released from reservoir 7 into the skin to be controlled by membranes of reasonable thickness, typically in the range of 0.001-0.003 inches. The membrane 3 may either be a solid membrane or a microporous membrane having rate controlling material in the micropores to meter the release of permeation enhancer 7. Typical rate controlling materials for the formation of a membrane per se or for the rate controlling material to be included in the pores of a microporous membrane would be hydrophobic materials such as polyethylene EVA, polycarbonates, polyvinyl chloride, polyacrylate polymers, polysulfone polymers, polyvinylidienes, polyvinylidenes, polyesters, and polyisobutylenes, for example.

The permeation enhancer may be present in the reservoir 7 either neat or as solution or dispersion thereof in an appropriate medium. The permeation enhancer can be selected from any of a wide variety of materials capable of enhancing skin permeation of ionic species. Typical materials include surfactants, such as the alkyl substituted sulfoxides such as n-octyl methyl sulfoxide, n-nonyl methyl sulfoxide, n-decylmethyl sulfoxide (n-DMS), n-undecyl methyl sulfoxide, n-dodecyl methyl sulfoxide; mono- and di-substituted alkyl polyethylene glycols such as polyethylene glycol mono laurate and polyethylene glycol di laurate; ethanol and other lower alcohols; n-methyl pyrrolidone, dimethyl lauramine, diethyltoluamide, and the 1-substituted azacycloalkan-2-ones disclosed in U.S. Pat. Nos. 3,989,816, 4,405,616, 4,415,563 and 4,424,210 which are incorporated herein by reference, for example.

Referring now to FIG. 2, another embodiment of the invention is shown. In this embodiment the transdermal therapeutic system 10 according to this invention comprises an impermeable backing 11 containing an aqueous, gelled drug reservoir 12. Reservoir 12 contains microcapsules 13 comprising the permeation enhancer encapsulated in a permeation enhancer release rate controlling material, drug 14, preferably at a level above saturation, and an appropriate buffer to maintain the pH in the physiological range. Highly permeable support layer 15 is bonded to the edges of backing 11, substantially in the same manner as described with respect to FIG. 1 to maintain the reservoir 12 within the system and provide substantially no resistance to the diffusion of the drug and the permeation enhancer therform. In this embodiment, if the viscosity of the gelled reservoir 12 is sufficiently high and the adhesive properties are sufficient to provide the bond strength to prevent reservoir 12 from falling out of receptacle 11 in use, layer 15 could be omitted. A contact adhesive 16 is provided in a peripheral ring below the perimeter of the backing member 11 such that the adhesive is capable of bonding the system to the skin without being in the path of drug and penmeation enhancer diffusion from the reservoir to the skin. In this embodiment the adhesive need not be porous. Below the adhesive is an impermeable release liner 17 adapted to protect the contents of the system and to be removed prior to application to the skin.

The materials used for the various components, with the exception of the contact adhesive, are substantially the same as described with respect to FIG. 1. Since the contact adhesive need not be porous and is not in line with the drug path, the constraints as to porosity and non-reactivity are less stringent and a wider selection of applicable materials is available.

Having thus generally described our invention, the following specific examples are provided.

EXAMPLES 1-5

Transdenmal delivery devices for the delivery of highly ionized, fat insoluble drugs as described in FIG. 1 are fabricated as set forth in Table I. (Percentages in weight %.) The systems can be fabricated in sizes of from 5 cm$^2$ to 40 cm$^2$. When applied to the chest of a patient, a steady state delivery rate in the ranges shown may be established after approximately 2-7 hours and maintained for the period shown.

TABLE 1

| TRANSDERMAL THERAPEUTIC SYSTEM FOR THE DELIVERY OF HIGHLY IONIZED, FAT INSOLUBLE DRUGS | | | |
|---|---|---|---|
| Example # | 1 | 2 | 3 |

TABLE 1-continued
TRANSDERMAL THERAPEUTIC SYSTEM FOR THE DELIVERY OF HIGHLY IONIZED, FAT INSOLUBLE DRUGS

| | | | |
|---|---|---|---|
| Backing | Polyester/EVA Laminate | Polyester/EVA Laminate | Medium Density Polyethylene/Polyester/EVA Trilaminate |
| Permeation Enhancer Reservoir | 50% n-DMS<br>50% EVA (40% VA)<br>Loading 60 mg/cm$^2$ | 50% n-DMS<br>50% EVA (40% VA)<br>Loading 60 mg/cm$^2$ | 50% n-DMS<br>50% EVA (40% VA)<br>Loading 40 mg/cm$^2$ |
| Rate Control Membrane | EVA (9% VA)<br>2 mil thickness | EVA (9% VA)<br>2 mil thickness | Low Density Polyethylene<br>1 mil thickness |
| Drug Reservoir | 30% naloxone HCl<br>3% hydroxypropyl cellulose (gellant)<br>67% water<br>Loading 30 mg/cm$^2$ | 30% nalbuphine HCl<br>3% cross-linked poly (acrylic acid)<br>67% water<br>Loading 30 mg/cm$^2$ | 25% phenylpropanolamine<br>4% hydroxyethyl cellulose<br>20% ethanol<br>51% water<br>Loading 20 mg/cm$^2$ |
| Support Membrane | Porous polypropylene<br>2 mil thick | Porous polypropylene<br>2 mil thick | Spun based EVA polyester |
| Adhesive | In-line porous polyacrylate adhesive | Circumferential dense acrylate adhesive | In-line porrous polyacrylate adhesive |
| Steady State In Vivo Release Rate | 25 μg/cm$^2$ hr<br>for 1-3 days | 30 μg/cm$^2$ hr<br>for 1-3 days | 20 μg/cm$^2$ hr<br>for 1-3 days |

| Example # | 4 | 5 |
|---|---|---|
| Backing | Medium Density Polyethylene/Polyester/EVA Trilaminate | Medium Density Polyethylene/Polyester/EVA Trilaminate |
| Permeation Enhancer Reservoir | 50 n-DMS<br>50% EVA (40% VA)<br>Loading 30 mg/cm$^2$ | 50% n-DMS<br>50% EVA (40% VA)<br>Loading 40 mg/cm$^2$ |
| Rate Control Membrane | EVA (12% VA)<br>2 mil thickness | EVA (12% VA)<br>2 mil thickness |
| Drug Reservoir | 8% chlorenaramine<br>5% hydropropylmethyl cellulose<br>85% water<br>Loading 25 mg/cm$^2$ | 35% phenylepher HCl<br>5% hydropropylmethyl cellulose<br>60% water<br>Loading 25 mg/cm$^2$ |
| Support Membrane | Spun based EVA/polyacrylate | Spun based EVA/polyester |
| Adhesive | In-line porous polyacrylate adhesive | In-Line porous polyacrylate adhesive |
| Steady State In Vivo Release Rate | 10 μg/cm$^2$ hr<br>for 1-3 days | 15 μg/cm$^2$ hr<br>for 1-3 days |

While our invention has been described with respect to several specific embodiments thereof, it is not to be construed as being limited thereto.

Various modifications will be apparent to workers skilled in the art which can be made without departing from the scope of this invention which is limited only by the following claims wherein we claim:

1. A medical device for the transdermal delivery of a highly ionized, fat insoluble drug comprising, in combination:
    a. aqueous drug reservoir means comprising at at least 50% water having said drug dissolved therein;
    b. receptacle means containing said reservoir means, said receptacle means being substantially impermeable to the contents of said reservoir means;
    c. highly permeable reservoir retaining means disposed over the the skin proximal surface of said aqueous reservoir means;
    d. permeation enhancer delivery means for delivering a permeation enhancer to the skin through said aqueous reservoir means, said permeation enhancer delivery means being disposed in permeation enhancer transferring relationship to said aqueous reservoir means and comprising:
        (i) a source of permeation enhancer, and
        (ii) permeation enhancer release rate controlling means disposed between said source of permeation enhancer and said aqueous reservoir means, said permeation enhancer release rate controlling means comprising a material permeable to said permeation enhancer and substantially impermeable to water and said drug; and
    e. means for maintaining said medical device in permeation enhancer and drug transmitting relationship to the skin.

2. The medical device of claim 1 wherein the pH of said aqueous reservoir is in the range of 4.5–8.5.

3. The medical device of claim 1 wherein said means for maintaining said medical device on the skin comprises a layer of a permeable adhesive disposed on the skin proximal surface of said reservoir retaining means.

4. The medical device of claim 1 wherein said permeation enhancer release rate controlling means comprises at least a portion of said receptacle means and said permeation enhancer is confined behind the skin distal surface of said receptacle means by an impermeable backing sealed to said receptacle means.

5. The medical device of claim 1 wherein said source of permeation enhancer comprises a multiplicity of microcapsules of permeation enhancer within said permeation enhancer release rate controlling means; said microcapsules being dispersed through said aqueous reservoir means.

6. The medical device of claim 1 wherein said aqueous reservoir means contains undissolved drug dispersed therethrough.

7. The medical device of claim 1 wherein said drug is dissolved within said aqueous reservoir means at a level below saturation.

8. The medical device of claim 1 wherein said means for maintaining said medical device on the skin comprises a peripherally disposed layer of adhesive outside the path of drug and permeation enhancer flow to the skin.

9. The medical device of claim 2 wherein said aqueous reservoir comprises a gel containing at least 50% water.

10. The medical device of claim 2 wherein said drug is selected from the group consisting of the ionized form of indomethacin, acetazolamide, methazolamide, acetylsalisylic acid, naltrexone, naloxone, nalbuphine, phenylephrine, chlorpheniramine, phenylpropanolamine, clonidine, dextromethorphan, atropine, fentanyl, apomorphine, propranolol, lidocaine, tetracycline, oxytetracycline, tetracaine, dibucaine, terbutaline, and brompheniramine.

11. The medical device of claim 10 wherein said aqueous reservoir comprises a gel containing at least 50% water.

12. The medical device of claim 2 wherein said permeation enhancer is selected from the group consisting of the alkyl substituted sulfoxides, mono and di-substituted alkyl polyethylene glycols, lower alkyl alcohols; n-methyl pyrrolidone, dimethyl lauramine, diethyltoleamide and 1-substituted azacycloalkan-2-ones.

13. The medical device of claim 2 wherein said drug is selected from the group consisting of ionized naloxone, nalbuphine, phenylpropanolamine, chlorphenaramine, and phenylepherine; said permeation enhancer is n-decylmethylsulfoxide and said permeation enhancer release rate controlling material is selected from the group consisting of ethylene vinyl acetate copolymers and polyethylene.

* * * * *